United States Patent [19]

Ernst et al.

[11] Patent Number: 5,710,048
[45] Date of Patent: Jan. 20, 1998

[54] DETERMINATION OF SURFACTANT CONCENTRATION IN AN AQUEOUS FLUID

[75] Inventors: Joseph M. Ernst; Harold J. Noble, Jr., both of Cincinnati, Ohio

[73] Assignee: Cincinnati Milacron Inc.

[21] Appl. No.: 706,871

[22] Filed: Sep. 3, 1996

[51] Int. Cl.$^6$ ................................................ G01N 31/16
[52] U.S. Cl. ........................... 436/119; 436/71; 436/163; 436/164
[58] Field of Search ............................ 436/17, 119, 163, 436/164

[56] References Cited

U.S. PATENT DOCUMENTS

| | | | |
|---|---|---|---|
| 3,969,076 | 7/1976 | Wang | 23/230 R |
| 3,992,149 | 11/1976 | Wang | 23/230 R |
| 5,389,546 | 2/1995 | Becket | 436/51 |

*Primary Examiner*—Robert J. Warden
*Assistant Examiner*—Sharidan Carrillo

*Attorney, Agent, or Firm*—John W. Gregg; Donald Dunn

[57] ABSTRACT

A single-phase method for quantitatively measuring the anionic surfactant content of an aqueous machining fluid is provided. The method is carried out at a pH value of from about 1.5 to about 3.0 and from about 9.5 to about 10.6 and involves the addition of an excess of a standardized aqueous solution of 1,3-didecyl-2-methylimidazolium chloride to the sample of aqueous machining fluid and then back titrating the excess 1,3-didecyl-2-methylimidazolium chloride with a standardized aqueous solution of polyvinylsulfuric acid potassium salt in the presence of toluidine blue indicator. Values of the amount of 1,3-didecyl-2-methylimidazolium chloride amount corresponding to anionic surfactant concentration are produced by conducting the method using a series of standard aqueous solutions containing anionic surfactant at known concentrations. These values are used to quantitatively determine the anionic surfactant content of a sample of aqueous machining fluid of unknown anionic surfactant concentration from measured values of 1,3-didecyl-2-methylimidazolium chloride obtained according to the method using the sample.

15 Claims, No Drawings

DETERMINATION OF SURFACTANT CONCENTRATION IN AN AQUEOUS FLUID

FIELD OF INVENTION

This invention relates to analytical methods for quantitatively determining the concentration of a constituent of an aqueous functional fluid. In particular, this invention pertains to analytical methods for measuring the concentration of anionic surfactants in aqueous based functional fluids. More particularly, this invention pertains to a single-phase titration method for quantitatively measuring the anionic surfactant content of an aqueous based functional fluid (e.g. a machining fluid).

BACKGROUND OF THE INVENTION

Aqueous based functional fluids include a broad spectrum of liquids, for example, machining fluids, hydraulic fluids, coolants and heat transfer fluids. The aqueous based machining fluids are extensively employed to mechanically shape metallic and non-metallic workpieces. Aqueous based hydraulic fluids are known to be used in transmitting and absorbing forces and have been known to be used in automotive shock absorbers. Water based machining fluids and hydraulic fluids are employed extensively in industry and commerce for their numerous safety, disposal and environmental advantages as well as cost advantages in many cases. Such machining fluids may be employed in cutting, grinding, turning, drilling, broaching, milling, extruding, punching, drawing and ironing, spinning and rolling processes to mechanically shape appropriate metal and non-metal workpieces (e.g. glass and ceramics). These aqueous based machining and hydraulic fluids are complex mixtures of a number of constituents, each of which perform one or more functions in the fluid. The same is true for other water based functional fluids. For example, water can serve as a primary carrier and a coolant. Organic lubricants in the aqueous functional fluid serve to reduce friction and heat production and reduce or prevent wear of contacting parts. Corrosion inhibitors present in the fluid may serve to reduce or prevent metallic, or in some cases non-metallic, corrosion or attack by the fluid contacting the metallic or non-metallic workpiece or part. Biocides and fungicides reduce or prevent microbial attack and deterioration of the fluid. Other components of the fluid may serve such other functions such as preventing foaming, precipitating metal contaminants and reducing or preventing misting. Aqueous based functional fluids, in particular aqueous based machining and hydraulic fluids, are known to contain surfactants (i.e. surface active agents). These surfactants can serve several functions including lubrication and the stable suspension of water insoluble constituents of the fluid.

Aqueous functional fluid compositions are known to change qualitatively and/or quantitatively with use, particularly extended use and with use under severe operating conditions (e.g. high temperatures and high forces). These changes may result from such factors as evaporation, reactions (e.g. oxidation), thermal degradation and physical degradation of various components of the composition. Additionally it has been known for aqueous functional fluids, such as aqueous based machining and hydraulic fluids, to deteriorate (i.e. adversely change chemically and/or physically) during storage, particularly storage at elevated temperatures and for extended periods. The chemical and/or physical changes in the aqueous based functional fluid during use and/or storage can lead to the reduced functional effectiveness of the fluid, loss of effective life of the fluid and problems such as, for example, increased wear (e.g. tool wear), increased friction, increased heat, increased microbial attack, increased corrosion, increased scrap production (e.g. in machining operations) and decreased stability. The last problem is especially significant in emulsion type aqueous functional fluids (e.g. emulsion type water based machining and hydraulic fluids). Break down of the emulsion can produce the loss of important constituents of the fluid. The deterioration of aqueous based functional fluids also has an economic impact on the fluid by reducing its cost effectiveness.

Controlling, combating and compensating for chemical and/or physical changes occurring in aqueous based functional fluids during use and/or storage is important to the economic and functional industrial and commercial utility of these fluids. In aqueous based machining fluids controlling, combating and compensating for chemical and/or physical changes in the fluid during use and/or storage is important to preserving the functional utility of the fluid, maximizing its useful life, and preventing adverse effects of friction and heat on the machining of metal and non-metal workpieces (e.g. problems of out of tolerance parts, distorted parts, poor surface finish and scrapped parts). In this regard, it is important to measure and monitor the content or concentration of various constituents of the aqueous based functional fluid during use and/or storage. Likewise, measurement of constituent concentration during manufacture is required to exercise quality control of the fluid produced.

The present invention relates generally to measurement and monitoring of concentration of constituents of aqueous functional fluids (e.g. machining and hydraulic fluids), and more particularly with measuring and monitoring the concentration of surfactants in aqueous functional fluids. Anionic surfactants are prevalent in, and often preferred in aqueous based machining fluid compositions, aqueous based hydraulic fluid compositions and other aqueous based functional fluid compositions. The anionic surfactant content of water based functional fluids (e.g. machining fluids) has been quantitatively measured by various methods in the prior art. In respect to aqueous based machining fluids, prior art quantitative analytical methods have predominately and preferably employed two-phase titration techniques for measuring anionic surfactant content because of the accuracy achieved with the technique.

A prior art water/organic solvent two-phase titration technique employs a water phase and an organic solvent phase. This technique involves titrating the anionic surfactant in a known amount of the aqueous based machining fluid (e.g. metalworking fluid) with a cationic titrant (e.g. cetyl trimethyl ammonium chloride) in the presence of a two-phase water/organic solvent (e.g. chloroform) medium and an indicator system (e.g. dimidium bromide/erioglaucine blue). In this method, a colored complex is formed during the titration, whose extraction into the organic solvent layer signals the endpoint of the titration. This same procedure is repeated using an aqueous solution of anionic surfactant having a known concentration of anionic surfactant in place of the aqueous based machining fluid. The amount of the aqueous cationic surfactant solution titrant used for the titration of the sample of machining fluid is compared to the amount of the same aqueous cationic surfactant solution titrant used for the titration of the aqueous anionic surfactant solution of known anionic surfactant concentration for calculating the amount of anionic surfactant (i.e. concentration of anionic surfactant) in the sample of aqueous based machining fluid. During the two-phase titration procedure, it is necessary to frequently shake the system to insure proper contact between and complete reaction of the surfactants, as well as dissolution of the color forming complex in the organic solvent layer. In this method, it is necessary that the organic solvent be essentially water insoluble. It is also necessary that the indicator form a complex with the cationic titrant that is essentially water insoluble and that is colored and soluble in the organic solvent. Where that color is distinguishable from any color the indicator may have in water.

The two-phase titration procedure, while providing acceptable results, has several disadvantages. For example, it is time consuming, requires frequent shaking, depends on how effective the shaking is in obtaining complete reaction between the cationic and anionic surfactants, requires the use of an organic solvent, has disposal problems for the organic solvent, may present health hazards in respect to the organic solvent and may be relatively expensive. Thus, it is desirable to have a reliable procedure for quantitatively measuring the anionic surfactant content of aqueous based functional fluids without the disadvantages of the two-phase procedure.

It is, therefore, an object of this invention to provide a procedure (i.e. method) of quantitatively measuring the anionic surfactant content of aqueous based functional fluids. Another object of this invention is to provide a method for quantitatively measuring the anionic surfactant content of aqueous based functional fluids overcoming disadvantages or drawbacks of the prior art water/organic solvent two-phase method for quantitatively measuring the anionic content of aqueous based functional fluids. A still further object of this invention is to provide a single-phase method for quantitatively measuring the anionic surfactant content of aqueous based machining and hydraulic fluids. An even further object of this invention is to provide a single-phase method for quantitatively measuring the anionic surfactant content of aqueous based functional fluids.

SUMMARY OF THE INVENTION

The above objects and others, as will be apparent to those skilled in the art from the following description and the appended claims, are accomplished in accordance with the single-phase quantitative analytical method of this invention. In accordance with this invention, there is provided a single-phase quantitative analytical method for measuring the anionic surfactant content of an aqueous based functional fluid. There is provided in this invention a single-phase method for quantitatively measuring the anionic surfactant content of an aqueous based functional fluid comprising the steps of a) adjusting the pH of the functional fluid to a value within a range of pH values selected from a group of pH value ranges, b) adding toluidine blue indicator to the functional fluid, c) adding a known amount of a standardized aqueous solution of 1,3-didecyl-2-methylimidazolium halide to a known amount of the aqueous based functional fluid in the presence of toluidine blue indicator, d) adding a standardized aqueous solution of polyvinylsulfuric acid alkali metal salt titrant in controlled known amounts until a blue to pink toluidine blue color change occurs, e) calculating the amount of 1,3-didecyl-2-methylimidazolium halide consumed by the anionic surfactant in the known amount of aqueous based functional fluid, f) preparing a pH range specific standard curve of the amount of reacted 1,3-didecyl-2-methylimidazolium halide vs. anionic surfactant concentration and g) comparing the consumed amount of 1,3-didecyl-2-methylimidazolium halide of step (e) with the standard curve produced in step (f) to establish the quantitative content of anionic surfactant in the aqueous based functional fluid. The term "aqueous functional fluid" as employed in this description and the appended claims shall mean a fluid comprising water and at least an organic lubricant and an anionic surfactant, and provides at least one of the functions of cooling, friction reduction, transmission of physical force and absorption of physical force. The phrase "standardized aqueous solution" as used in this description and the appended claims shall mean a solution having a known concentration of the constituent identified with the solution. The phrase "single-phase" as used in this description and the appended claims shall mean a water titration system free of added organic solvent.

DESCRIPTION OF THE INVENTION

There has now been discovered a single-phase titration method for quantitatively measuring the anionic surfactant content of an anionic surfactant containing functional fluid that overcomes disadvantages found in the commonly employed two-phase method for measuring anionic surfactant concentration in such fluids. In accordance with this invention there is provided (I) a single-phase method for quantitatively measuring the anionic surfactant content of an aqueous based functional fluid comprising water and at least an organic lubricant and an anionic surfactant selected from the group consisting of sulfonate anionic surfactants and fatty acid anionic surfactants comprising the steps of a) adjusting the pH of the aqueous based functional fluid to a value within a range selected from the group of pH ranges consisting of pH ranges of from about 1.5 to about 3.0 and from about 9.5 to 10.6, b) adding toluidine blue indicator to the aqueous based functional fluid, c) adding a known amount of a standardized aqueous solution of 1,3-didecyl-2-methylimidazolium halide of known concentration to a known amount of the pH adjusted functional fluid, d) adding a standardized aqueous solution of polyvinylsulfuric acid alkali metal salt titrant of known concentration in controlled known amounts until a blue to pink toluidine blue indicator color change occurs, e) observing the total amount the titrant used in step (d), f) calculating the amount of 1,3-didecyl-2-methylimidazolium halide consumed by the polyvinylsulfuric acid alkali metal salt from the known amounts of the aqueous solution of 1,3-didecyl-2-methylimidazolium halide and the aqueous solution of polyvinylsulfuric acid alkali metal salt employed in steps (c) and (d) and the respective known concentrations thereof, g) subtracting the amount of 1,3-didecyl-2-methylimidazolium halide of step (f) from the amount of 1,3-didecyl-2-methylimidazolium halide employed in step (c) to obtain a reaction value of 1,3-didecyl-2-methylimidazolium halide, h) preparing a pH range specific standard curve or plot of 1,3-didecyl-2-methylimidazolium halide amount vs. anionic surfactant concentration using a series of aqueous anionic surfactant solutions having known concentrations of the anionic surfactant and steps (a) to (g) above wherein the aqueous solution of artionic surfactant is substituted for the aqueous based functional fluid and i) comparing the reaction value amount of 1,3-didecyl-2-methylimidazolium halide with the pH range specific standard plot having a range of pH corresponding to the range of pH to which the pH of the aqueous functional fluid was adjusted.

In one embodiment of this invention there is provided (II) a single-phase method for quantitatively measuring the sulfonate anionic surfactant content of an aqueous based functional fluid comprising water and at least a sulfonate artionic surfactant and an organic lubricant comprising the steps of a) adjusting the pH of the aqueous based functional fluid to a value within the range of about 1.5 to about 3.0, b) adding toluidine blue indicator to the aqueous based functional fluid, c) adding a known amount of a standardized aqueous solution of 1,3-didecyl-2-methylimidazolium halide of known concentration to a known amount of the aqueous based functional fluid, d) adding a standardized aqueous solution of polyvinylsulfuric acid alkali metal salt titrant of known concentration in controlled known amounts until a blue to pink toluidine blue indicator color change occurs, e) observing the total amount of the titrant used in step (d), f) calculating the amount of 1,3-didecyl-2-methylimidazolium halide consumed by the polyvinylsulfuric acid alkaline metal salt from the known amounts of the aqueous solution of 1,3-didecyl-2-methylimidazolium halide and the aqueous solution of polyvinylsulfuric acid alkali metal salt employed in steps (c) and (d) and the respective known concentrations thereof, g) subtracting the amount of 1,3-didecyl-2-methylimidazolium halide of step (f) from the amount of 1,3-didecyl-2-methylimidazolium halide employed in step (c) to obtain a reaction value of 1,3-didecyl-2-methylimidazolium halide, h) preparing a pH range specific standard plot of 1,3-didecyl-2-methylimidazolium halide amount vs. sulfonate artionic surfactant for a pH range of from about 1.5 to about 3.0 using a series of aqueous sulfonate anionic surfactant solutions having known concentrations of sulfonate anionic surfactant and steps (a) to (g) above wherein the aqueous sulfonate artionic surfactant solution is substituted for the aqueous based functional fluid and i) comparing the reaction value amount of 1,3-didecyl-2-methylimidazolium halide with the pH range specific standard plot produced in step (h) to establish the quantitative content of the sulfonate anionic surfactant in the aqueous based functional fluid.

As another embodiment of this invention there is provided (III) a single-phase method for quantitatively measuring the fatty acid anionic surfactant content of an aqueous based functional fluid comprising water and at least a fatty acid artionic surfactant and an organic lubricant comprising the steps of a) adjusting the pH of the aqueous based functional fluid to a value within the range of about 9.5 to about 10.6, b) adding toluidine blue indicator to the aqueous functional fluid, c) adding a known amount of a standardized alkaline aqueous solution of 1,3-didecyl-2-methylimidazolium halide of known concentration to a known amount of the aqueous based functional fluid, d) adding a standardized aqueous solution of polyvinylsulfuric acid alkali metal salt titrant of known concentration in controlled known amounts until a blue to pink toluidine blue indicator color change occurs, e) observing the total amount of the titrant used in step (d), f) calculating the amount of 1,3-didecyl-2-methylimidazolium halide consumed by the polyvinylsulfuric acid alkali metal salt from the known amounts of the aqueous solution of 1,3-didecyl-2-methylimidazolium halide and the aqueous solution of polyvinylsulfuric acid alkali metal salt employed in steps (c) and (d) and the respective known concentrations thereof, g) subtracting the amount of 1,3-didecyl-2-methylimidazolium halide of step (f) from the amount of 1,3-didecyl-2-methylimidazolium halide employed in step (c) to obtain a reaction value of 1,3-didecyl-2-methylimidazolium halide, h) preparing a pH range specific standard plot of 1,3-didecyl-2-methylimidazolium halide amount vs. fatty acid artionic surfactant concentration for a range of pH from about 9.5 to about 10.6 using a series of aqueous fatty acid anionic surfactant solutions having known concentrations of the fatty acid anionic surfactant and steps (a) to (g) above wherein the aqueous fatty acid anionic surfactant solution is substituted for the aqueous based functional fluid and i) comparing the reaction value amount of 1,3-didecyl-2methylimidazolium halide with the pH range specific standard plot produced in step (h) to establish the quantitative content of the fatty acid surfactant in the aqueous based functional fluid.

In the practice of the methods of (I), (II) and (III) above, there may be employed an aqueous functional fluid selected from the group consisting of aqueous based machining fluids and aqueous based hydraulic fluids. Thus, in a practice of the method of (I) above, the aqueous based functional fluid may be an aqueous based machining fluid comprising, in addition to water, at least an anionic surfactant and an organic lubricant while in another practice of the method of (I) above the aqueous based functional fluid may be an aqueous based hydraulic fluid comprising, in addition to water at least an anionic surfactant and an organic lubricant. In a practice of the method of (II) above, the aqueous based functional fluid may be an aqueous based machining fluid comprising, in addition to water, at least a sulfonate anionic surfactant and an organic lubricant while in another practice of the method of (II) above the aqueous based functional fluid may be an aqueous based hydraulic fluid comprising, in addition to water, at least a sulfonate anionic surfactant and an organic lubricant. In respect to the method of (III) above, there may be employed as the aqueous based functional fluid an aqueous based machining fluid comprising, in addition to water, at least a fatty acid anionic surfactant and an organic lubricant or there may be used as the aqueous based functional fluid an aqueous based hydraulic fluid comprising, in addition to water, at least a fatty acid anionic surfactant and an organic lubricant. There may be employed in the practice of the methods of (I), (II) and (III) above as the 1,3-didecyl-2-methylimidazolium halide, 1,3-didecyl-2-methylimidazolium fluoride, 1,3-didecyl-2-methylimidazolium bromide, 1,3-didecyl-2-methylimidazolium chloride or 1,3-didecyl-2-methylimidazolium iodine. Preferably 1,3-didecyl-2-methylimidazolium chloride is used in the methods of (I), (II) and (III) above. The polyvinylsulfuric acid alkali metal salt employed in the methods of (I), (II) and (III) above may be polyvinylsulfuric acid lithium salt, polyvinylsulfuric acid sodium salt or preferably polyvinylsulfuric acid potassium salt.

There is provided in accordance with this invention a single-phase method for quantitatively measuring the anionic surfactant content of an aqueous based machining fluid comprising water, and at least an anionic surfactant and an organic lubricant comprising the steps of a) adjusting the pH of the aqueous based machining fluid to a value within a range selected from the group consisting of pH ranges of from about 1.5 to about 3.0 and from about 9.5 to about 10.6, b) adding toluidine blue indicator to the aqueous based machining fluid, c) adding a known amount of a standardized aqueous solution of 1,3-didecyl-2-methylimidazolium chloride of known concentration to a known amount of the aqueous based machining fluid, d) adding a standardized aqueous solution of polyvinylsulfuric acid potassium salt titrant of known concentration in controlled known amounts until a blue to pink toluidine blue indicator color change occurs, e) observing the total amount of the aqueous solution of polyvinylsulfuric acid potassium salt titrant added to obtain the blue to pink toluidine blue indicator color change in step (d), f) calculating the amount of 1,3-didecyl-2-methylimidazolium chloride consumed by the polyvinylsulfuric acid potassium salt from the known amounts of the aqueous solution of 1,3-didecyl-2-methylimidazolium chloride and the aqueous solution of polyvinylsulfuric acid potassium salt employed in steps (c) and (d) and the respective known concentrations thereof, g) subtracting the amount of 1,3-didecyl-2-methylimidazolium chloride of step (f) from the amount of 1,3-didecyl-2-methylimidazolium chloride employed in step (c) to obtain a reaction value of 1,3-didecyl-2-methylimidazolium chloride, h) preparing a pH range specific standard plot of 1,3-didecyl-2-methylimidazolium chloride amount vs. anionic surfactant concentration using a series of aqueous anionic surfactant solutions having known concentrations of anionic surfactant and steps (a) to (g) above for the ranges of pH corresponding to the ranges of pH to which the pH of the machining functional fluid was adjusted wherein the aqueous anionic surfactant solutions are substituted for the aqueous based machining fluid and i) comparing the reaction value amount of 1,3-didecyl-2-methylimidazolium chloride of step (g) with the pH range specific standard plot of step (h) for the same pH range selected in step (a) to establish the quantitative pH range specific anionic surfactant content of the aqueous machining fluid.

In accordance with this invention there is provided a single-phase method for quantitatively measuring the sulfonate anionic surfactant content of an aqueous based machining fluid comprising water and at least a sulfonate anionic surfactant and an organic lubricant comprising the steps of a) adjusting the pH of the aqueous based machining fluid to a value within the range of about 1.5 to about 3.0, b) adding toluidine blue indicator to the aqueous based machining fluid, c) adding a known amount of a standardized aqueous solution of 1,3-didecyl-2-methylimidazolium chloride to a known amount of the aqueous based machining fluid, d) adding a standardized aqueous solution of polyvinylsulfuric acid potassium salt titrant in controlled known amounts until a blue to pink toluidine blue indicator color change occurs, e) observing the total amount of the aqueous polyvinylsulfuric acid potassium salt titrant added to obtain the blue to pink toluidine blue indicator color change in step (d), f) calculating the amount of 1,3-didecyl-2-methylimidazolium chloride consumed by the polyvinylsulfuric acid potassium salt from the known amounts of the aqueous solution of 1,3-didecyl-2methylimidazolium chloride and the aqueous solution of polyvinylsulfuric acid potassium salt employed in steps (c) and (d) and their known concentrations of 1,3-didecyl-2methylimidazolium chloride and polyvinylsulfuric acid potassium salt respectively, g) subtracting the amount of 1,3-didecyl-2-methylimidazolium chloride of step (f) from the amount of 1,3-didecyl-2-methylimidazolium chloride employed in step (c) to obtain a reaction value for the 1,3-didecyl-2-methylimidazolium chloride, h) preparing a pH range of about 1.5 to about 3.0 pH specific standard plot of 1,3-didecyl-2-methylimidazolium chloride amount vs. sulfonate anionic surfactant concentration using a series of aqueous sulfonate artionic surfactant solutions of known sulfonate anionic surfactant concentrations and steps (a) to (g) above wherein the aqueous sulfonate surfactant solutions are substituted for the aqueous based machining fluid and i) comparing the reaction value amount of 1,3-didecyl-2-methylimidazolium chloride of step (g) with the pH specific standard plot produced in step (h) to establish the quantitative sulfonate anionic surfactant content of the aqueous based machining fluid.

As a further embodiment of this invention there is provided a single-phase method for quantitatively measuring the fatty acid anionic surfactant content of an aqueous based machining fluid comprising water and at least a fatty acid anionic surfactant and an organic lubricant comprising the steps of a) adjusting the pH of the aqueous machining fluid to a value within the range of from about 9.5 to about 10.6, b) adding toluidine blue indicator to the aqueous based machining fluid, c) adding a known amount of a standardized aqueous solution of 1,3-didecyl-2-methylimidazolium chloride to a known amount of the aqueous based machining fluid, d) adding a standardized aqueous solution of polyvinylsulfuric acid potassium salt titrant in controlled known amounts until a blue to pink toluidine blue indicator color change occurs, e) observing the total amount of the aqueous polyvinylsulfuric acid potassium salt titrant added to obtain the blue to pink toluidine blue color change in step (d), f) calculating the amount of 1,3-didecyl-2-methylimidazolium chloride consumed by the polyvinylsulfuric acid potassium salt from the known amounts of the aqueous solution of 1,3-didecyl-2-methylimidazolium chloride and the aqueous solution of polyvinylsulfuric acid potassium salt employed in steps (c) and (d) and their known concentrations of 1,3-didecyl-2-methylimidazolium chloride and polyvinylsulfuric acid potassium salt respectively, g) subtracting the amount of 1,3-didecyl-2-methylimidazolium chloride of step (f) from the amount of 1,3-didecyl-2-methylimidazolium chloride employed in step (c) to obtain a reaction value for the 1,3-didecyl-2-methylimidazolium chloride, h) preparing a pH range of about 9.5 to about 10.6 pH standard plot of 1,3-didecyl-2-methylimidazolium chloride amount vs. fatty acid artionic surfactant concentration using a series of aqueous fatty acid anionic surfactant solutions of known fatty acid anionic surfactant concentrations and steps (a) to (g) above wherein the aqueous fatty acid anionic surfactant solutions are substituted for the aqueous based machining fluid and i) comparing the total amount of 1,3-didecyl-2-methylimidazolium chloride of step (g) with the pH range of about 9.5 to about 10.6 pH specific standard plot produced in step (h) to establish the quantitative fatty acid anionic surfactant content of the aqueous based machining fluid.

A pH specific standard curve or plot of 1,3-didecyl-2-methylimidazolium chloride amount vs. concentration of anionic surfactant concentration may be prepared in the following manner. A series of aqueous anionic surfactant solutions of known anionic surfactant concentration using a sulfonate anionic surfactant, or a fatty acid anionic surfactant are prepared. A sample of the aqueous anionic surfactant solution is adjusted to a pH value within the range of about 1.5 to about 3.0 with aqueous hydrochloric acid for the aqueous sulfonate anionic surfactant solution or to a pH value within the range of about 9.5 to about 10.6 with aqueous potassium hydroxide for the aqueous fatty acid anionic surfactant solution. Toluidine blue indicator is then added to the aqueous anionic surfactant solution. To a known amount of the aqueous anionic surfactant solution as so prepared, is added a standardized aqueous solution of 1,3-didecyl-2-methylimidazolium chloride in a known amount and in excess of the stoichiometric amount of 1,3-didecyl-2-methylimidazolium chloride needed to react with all of the anionic surfactant in the aqueous anionic surfactant solution. This system is then titrated with a standardized aqueous solution of polyvinylsulfuric acid potassium salt to a blue to pink toluidine blue indicator color change endpoint. The amount of 1,3-didecyl-2-methylimidazolium chloride reacted with the polyvinylsulfuric acid potassium salt is calculated from the known amounts of the aqueous solutions of these materials used and their known concentrations. The amount of 1,3-didecyl-2-methylimidazolium chloride consumed by the polyvinylsulfuric acid potassium salt during the titration is subtracted from the original amount of 1,3-didecyl-2-methylimidazolium chloride added to the known amount of aqueous anionic surfactant solution of known concentration to determine the amount of 1,3-didecyl-2-methylimidazolium chloride that reacted with the anionic surfactant. That resultant amount of 1,3-didecyl-2-methylimidazolium chloride is then plotted against the concentration of the anionic surfactant. This process is repeated for each of the aqueous anionic surfactant solutions of the series of aqueous solutions of known anionic surfactant concentration. The above procedure would be applicable where other 1,3-didecyl-2-methylimidazolium halides and other polyvinylsulfuric acid alkali salts would be used instead of 1,3-didecyl-2-methylimidazolium chloride and polyvinylsulfuric acid potassium salt. It is to be recognized and is contemplated in the practice of this invention that the step of preparing a pH specific standard plot of 1,3-didecyl-2-methylimidazolium halide amount vs. concentration of anionic surfactant need not be carried out each time the method is performed. Rather the standard plot may be prepared prior to carrying out the method of this invention and employed in successive measurements of the anionic surfactant concentration of different samples of aqueous based functional fluids.

Aqueous based functional fluids, especially aqueous based machining fluids (e.g. metalworking fluids) become contaminated with various materials during use. These materials may include for example, solid particles, contaminating oils and breakdown products in the fluids. As a consequence of such contamination, the fluid often becomes discolored and/or turbid. To overcome such discoloration and/or turbidity it is often desirable to dilute such used fluids when employing the method of this invention to quantitatively measure the artionic surfactant content of the functional fluid. Such dilution is of course to be done in a known manner with analytical precision using water. These dilutions may also be carried out to adjust the concentrations of functional fluid to levels that would require the use of lesser amounts of reagents in carrying out the method of this invention. The dilutions of the aqueous based functional fluids do not adversely effect the method of this invention nor the accuracy of the result when done with analytical precision and must be taken into account, in manners well known to those skilled in the art, when making the calculation of the artionic content of the functional fluid.

Adjunct endpoint color change enhancers may be employed in the practice of this invention, especially when quantitatively measuring the anionic surfactant content of heavily contaminated and/or dark colored aqueous based function fluids (e.g. aqueous based metalworking fluids) without adversely affecting the accuracy of the results obtained in accordance with the method of this invention. Such titration endpoint color change enhancers are particularly useful where the colorproduced at the endpoint is light in shade. Examples of such titration endpoint color change enhancers include but are not limited to CHROMATINT Red 0551 obtainable from Chromatech Inc. and thymol blue. CHROMATINT is a registered trademark of Chromatech Inc.

In accordance with this invention, the pH of the aqueous functional fluid is adjusted to a value within the range of a selected pH range. The pH of the adjusted aqueous based functional fluid may be measured by methods well known in the art, such as, for example pH meters, litmus papers and pH indicator dyes. In the practice of this invention the step of adjusting the pH of the functional fluid to a value within a range of from about 1.5 to about 3.0 is preferably accomplished using a mineral acid and in the range from about 9.5 to about 10.6 is preferably accomplished using an alkali metal hydroxide.

This invention has been described and claimed with respect to an order of method steps. However, in the practice of this invention, the order of the method steps of adjusting the pH of the functional fluid to a value within a range selected from a group consisting of pH ranges, adding toluidine blue indicator to the functional fluid and adding a known amount of a standardized aqueous solution of 1,3-didecyl-2-methylimidazolium halide to a known amount of functional fluid may be varied. Thus, for example, the standardized aqueous solution of 1,3-didecyl-2-methylimidazolium halide may be added to the aqueous functional fluid before the step of adjusting the pH of the functional fluid or the toluidine blue indicator may be added after the addition of the aqueous solution of 1,3-didecyl-2-methylimidazolium halide. In the practice of this invention, it may be desirable to combine the toluidine blue indicator with the aqueous solution of 1,3-didecyl-2-methylimidazolium halide and add the resulting combination to the aqueous based functional fluid before or even after adjusting the pH of the functional fluid.

In accordance with the invention described herein, and claimed in the appended claims, the aqueous functional fluid of the method comprises in addition to water at least an organic lubricant and an anionic surfactant selected from the group consisting of fatty acid anionic surfactants and sulfonate anionic surfactants. It is well known in the art that a constituent of an aqueous based functional fluid (e.g. aqueous based machining fluid) may have or exhibit more than one function in the fluid. The surfactant may in some cases not only exhibit surface active behavior for dispersing insoluble constituents in the fluid but may also exhibit some degree of lubrication behavior (i.e. may function to some degree as a lubricant). Thus in accordance with the method of this invention, as described herein and claimed in the appended claims, the terms lubricant and surfactant set forth or describe materials as well as functions and that such functions may be exhibited by the same constituent. It is therefore contemplated that the anionic surfactant constituent of the aqueous based functional fluid of the method of this invention may also be the organic lubricant constituent of said aqueous based functional fluid.

In contrast to prior art two-phase methods for quantitatively measuring the anionic surfactant content of aqueous machining fluids, wherein there is employed a combination of water and an organic solvent, the method of this invention, as described herein and claimed in the appended claims, is a single-phase method for quantitatively measuring the anionic surfactant content of aqueous based machining fluids and other aqueous based functional fluids wherein water is employed as the single-phase and an organic solvent is not used in the method. Thus the problems associated with the organic solvent (e.g. health hazards and disposal problems) and the achieving of sufficient mixing of water and the organic solvent in the prior art two-phase methods are avoided in the method of this invention.

This invention may be further described with reference to the following procedure.

Anionic Surfactant Concentration Determination

REAGENTS AND APPARATUS 1,3-didecyl-2-methylimidazolium chloride (TEGOtrant A-100)Brinkman Instruments, Inc. 020-95-928-2

Polyvinyl Sulfuric Acid, Potassium salt (PVSK)—Aldrich 27196-9

Toluidine Blue—Fisher T-161

Thymol Blue -Aldrich 86136-7

Sodium Lauryl Sulfate (SLS)—Aldrich 86201-0

Potassium Hydroxide (KOH)—Fisher P250-1;

Hydrochloric Acid (HCL), 0.1N—Fisher SA54-20

NS Blue Solution

NS Red #1 Solution

NS Red #2 Solution

Chromatint Red 0551—Chromatech Inc.

Buret, 25 ml.

Pipettes, capable of measuring from 0.1 to 10 ml.

Edenmeyer Flasks, 125 ml.

Volumetric Flasks, 250 ml., 500 ml., 1 liter

Analytical Balance, capable of weighing to +/−0.5 mg.

Magnetic stirrer

REAGENTS AND APPARATUS (Cont'd)

Stirring bars

Dispensers, capable of dispensing 20 ml.

Graduated Cylinder, 100 ml.

PROCEDURE

Reagent Preparation 1) 0.004 M TEGOtrant—weigh 1.68 g of TEGOtrant, dissolve in (DI) deionized water and dilute to I liter with DI water. Let stand for 24 hrs. Add 10 ml of 0.002 M SLS to a 125 Edenmeyer Flask. Add 90 ml of DI water and I ml of Toluidine Blue solution (0.3 g/l) to the flask. Titrate the SLS with the aged TEGOtrant solution to a blue endpoint. (Indicator changes from purple-blue to pink to blue). A titer of 4.5 ml to 5.5 ml indicates that the TEGOtrant is at the proper strength. If not, adjust the solution accordingly.

2) PVSK Titrant—weigh 0.20 g of PVSK, dissolve in DI water and dilute to 1 liter with DI water. Run a blank titration, using the fresh PVSK solution, according to the Steps 1a, 2–4 of the Blank Titration procedure below. A titer of 13.5 ml to 15.5 ml indicates that the PVSK is at the proper strength. If not, adjust the solution accordingly.

3) Toluidine Blue—weigh 0.3 g of Toluidine Blue, dissolve in DI water and dilute to 1 liter with DI water.

4) 0.002 M SLS—weigh 0.1440 g of SLS, dissolve in DI water and dilute to 250 ml with DI water.

5) 1 M KOH—weigh 56.11 g of KOH, dissolve in DI water and dilute to 1 liter with DI water.

6) NS Blue Solution—measure 97 ml of 0.004 M TEGOtrant and 33.8 ml of 0.3g/l of Toluidine Blue and dilute to 1 liter with DI water. Titrate this solution using steps 1a, 2–4 of the *Blank Titration* procedure. A titer of 13.5 ml to 15.5 ml indicates that the NS Blue solution is at the proper strength. If not, adjust accordingly.

7) NS Red #1 Solution—Dissolve 0.07 g of Thymol Blue in 0.1 NHCl and dilute to 1 liter with 0.1 N HCl.

8) NS Red #2—weigh 3.0 g of Chromatint Red 0551, dissolve in DI water and dilute to 500 ml with DI water.

Blank Titration:. (A Blank titration preferably should be run daily or whenever a new lot of TEGOtrant or PVSK is used)

1a) For free fatty acid (FFA) anionic surfactant concentration determinations at a pH in the range of from about 9.5 to about 10.6, add 20 ml of NS Blue Solution, 0.1 ml of 1 M KOH, 5 drops of NS Red #2 Solution and 80 ml of DI water to a 125 Edenmeyer flask containing a stirring bar.

1b) For sulfonate anionic surfactant concentration determination at a pH in the range of from about 1.5 to about 3.0, add 20 ml of NS Blue Solution, 20 ml of NS Red #1 and 60 ml of DI water to a 125 ml Edenmeyer flask containing a stirring bar.

2) Place the flask on the magnetic stirrer, stir at a moderate rate, and rapidly add PVSK titrant until the purple-blue color (for FFA anionic surfactant) or the blue-green color (for sulfonates anionic surfactant) begins to turn to pink. At this point, slow the addition of titrant to approximately one drop per second.

3) When the color of the solution has turned to pink, stop the addition of titrant. The color should hold for at least 10 seconds if the end-point has been reached. If the color fades, add 1–2 more drops of PVSK.

4) Record the volume (mls) of PVSK used as the blank value. Standardization: [The standardization procedure may under some circumstances (e.g. using fresh aqueous metalworking fluid of known anionic surfactant concentration) be conducted or repeated at regular intervals (e.g. 3 months) to insure consistency and control in the method for measuring anionic surfactant concentration of unknown samples.]

1) Prepare standard mixes of the appropriate anionic surfactant at 2%, 4%, 6% and 8% concentration in tap water. Standard mixes at appropriate anionic surfactant concentrations may be also prepared by preparing known dilutions of fresh aqueous metalworking fluid of known anionic surfactant concentration.

2a) For FFA anionic surfactant concentration determination at a pH in the range of from about 9.5 to about 10.6 add 20 ml of NS Blue Solution, 0.1 ml of 1 M KOH, 5 drops of Red #2 Solution and 80 ml of DI water to a 125 ml Edenmeyer flask containing a stirring bar.

2b) For sulfonate anionic surfactant concentration determinations at a pH in the range of from about 1.5 to about 3.0 add 20 ml of NS Blue Solution, 20 mls of NS Red #1 Solution and 60 ml of DI water to a 125 Edenmeyer flask containing a stirring bar.

3) Pipette the appropriate amount of standard mix into the flask.

4) Place the flask on the stirrer and rapidly add PVSK titrant until the purple-blue color (for FFA anionic surfactant) or the blue-green color (for sulfonate anionic surfactant) begins to turn pink. At this point, slow the addition of titrant to approximately one drop per second.

5) When the color has turned to pink, stop the addition of titrant. The color should hold for at least 10 seconds if the end-point has been reached. If the color fades, add 1–2 more drops of PVSK.

6) Record the volume (ml) of titrant used. Repeat steps 2–6 for each standard mix.

7) Perform a linear regression on the data (using Excel or any comparable software program) where the titer for each standard is:

titer=Blank titer−sample titer

The linear equation will give the slope and y-intercept to be used in calculating the % concentration of unknowns. A Factor can be obtained by forcing the line through zero. This Factor can then be used to determine the concentration of unknowns.

Titrating Unknowns

1) Determine the appropriate sample size to be used.

2) Follow steps 2–6 under Standardization: using the sample in place of the standard mix.

3) Calculate the % anionic surfactant concentration of each unknown (i.e. sample) as follows: using the linear regression formula:

% Concentration=slope×(Blank titer−sample titer)+intercept or, using the Factor:

% Concentration=Factor×(Blank titer−sample titer)

We claim:

1. In a single-phase method for quantitatively measuring the anionic surfactant content of an aqueous based functional fluid comprising water and at least an organic lubricant and an anionic surfactant selected from the group consisting of sulfonate anionic surfactants and fatty acid anionic surfactants the steps comprising:

a) adjusting the pH of the functional fluid to a value within a range selected from the group consisting of pH ranges of from about 1.5 to about 3.0 and from about 9.5 to about 10.6;

b) adding toluidine blue indicator to the functional fluid;

c) adding a known amount of a standardized aqueous solution of 1,3-didecyl-2methylimidazolium halide of known concentration to a known amount of the functional fluid;

d) adding a standardized aqueous solution of polyvinylsulfuric acid alkali metal salt titrant of known concentration in controlled known amounts until a blue to pink toluidine blue indicator color change occurs;

e) observing the total amount of the standardized aqueous solution of polyvinylsulfuric acid alkali metal salt titrant added in step (d);

f) calculating the amount of 1,3-didecyl-2-methylimidazolium halide consumed by the polyvinylsulfuric acid alkali metal salt from the known amounts of the aqueous solution of 1,3-didecyl-2-methylimidazolium halide and the aqueous solution of polyvinylsulfuric acid alkali metal salt employed in steps (c) and (d) and the respective known concentrations thereof;

g) subtracting the amount of 1,3-didecyl-2-methylimidazolium halide of step (f) from the amount of 1,3-didecyl-2-methylimidazolium halide employed in step (c) to obtain a reaction value of 1,3-didecyl-2-methylimidazolium halide;

h) preparing a pH range specific standard curve of reaction value of 1,3-didecyl-2-methylimidazolium halide vs. anionic surfactant concentration for pH ranges of from about 1.5 to about 3.0 and from about 9.5 to about 10.6, and i) comparing the reaction value of 1,3-didecyl-2-methylimidazolium halide with a pH range specific standard curve for a range of pH corresponding to the range of pH to which the pH of the functional fluid was adjusted to establish the pH range specific anionic surfactant content of the fluid.

2. In a single-phase method for quantitatively measuring the sulfonate anionic surfactant content of an aqueous based functional fluid comprising water, and at least an organic lubricant and a sulfonate anionic surfactant the steps comprising:

a) adjusting the pH of the functional fluid to a value within the range of from about 1.5 to about 3.0;

b) adding toluidine blue indicator to the functional fluid;

c) adding a known amount of a standardized aqueous solution of 1,3-didecyl-2-methylimidazolium halide of known concentration to a known amount of the functional fluid;

d) adding a standardized aqueous solution of polyvinylsulfuric acid alkali metal salt lo titrant of known concentration in controlled known amounts until a blue to pink toluidine blue indicator color change occurs;

e) observing the total amount of the standardized aqueous solution of polyvinylsulfuric acid alkali metal salt titrant added in step (d);

f) calculating the amount of 1,3-didecyl-2-methylimidazolium halide consumed by the polyvinylsulfuric acid alkali metal salt from the known amounts of the aqueous solution of 1,3-didecyl-2-methylimidazolium halide and the aqueous solution of polyvinylsulfuric acid alkali metal salt employed in steps (c) and (d) and the respective known concentrations thereof;

g) subtracting the amount of 1,3-didecyl-2-methylimidazolium halide of step (f) from the amount of 1,3-didecyl-2-methylimidazolium halide employed in step (c) to obtain a reaction value of 1,3-didecyl-2-methylimidazolium halide;

h) preparing a pH range specific standard curve of reaction value amount for 1,3-didecyl-2-methylimidazolium halide vs. sulfonate anionic surfactant concentration for a range of pH from about 1.5 to about 3.0; and i) comparing the reaction value of 1,3-didecyl-2-methylimidazolium halide with the pH range specific standard curve to establish the sulfonate anionic surfactant content of the functional fluid.

3. In a single-phase method for quantitatively measuring the fatty acid anionic surfactant content of an aqueous based functional fluid comprising water and at least an organic lubricant and a fatty acid anionic surfactant the steps comprising:

a) adjusting the pH of the functional fluid to a value within the range of from about 9.5 to about 10.6;

b) adding toluidine blue indicator to the functional fluid;

c) adding a known amount of a standardized aqueous solution of 1,3-dimethyl-2-methylimidazolium halide of known concentration to a known amount of the functional fluid;

d) adding a standardized aqueous solution of polyvinylsulfuric acid alkali metal salt titrant of known concentration in controlled known amounts until a blue to pink toluidine blue indicator color change occurs;

e) observing the total amount of the standardized aqueous solution of polyvinylsulfuric acid alkali metal salt titrant added in step (d);

f) calculating the amount of 1,3-didecyl-2-methylimidazolium halide consumed by the polyvinylsulfuric acid alkali metal salt from the known amounts of the aqueous solution of 1,3-didecyl-2-methylimidazolium halide and the aqueous solution of polyvinylsulfuric acid alkali metal salt employed in steps (c) and (d) and the respective known concentrations thereof;

g) subtracting the amount of 1,3-didecyl-2-methylimidazolium halide of step (f) from the amount of 1,3-didecyl-2-methylimidazolium halide employed in step (c) to obtain a reaction value of 1,3-didecyl-2-methylimidazolium halide;

h) preparing a pH range specific standard curve of reaction value amount for 1,3-didecyl-2-methylimidazolium halide vs. fatty acid anionic surfactant concentration for a range of pH from about 9.6 to about 10.5; and i) comparing the reaction value of 1,3-didecyl-2-methylimidazolium halide with the pH range specific standard curve to establish the fatty acid anionic surfactant content of the functional fluid.

4. The method of claim 1 wherein the fluid is selected from the group consisting of an aqueous based machining fluid and an aqueous based hydraulic fluid.

5. The method of claim 4 wherein the halide is chloride and the alkali metal is potassium.

6. The method of claim 5 wherein the fluid is an aqueous based machining fluid.

7. The method according to claim 2 wherein the fluid is selected from the group consisting of an aqueous based machining fluid and an aqueous based hydraulic fluid.

8. The method according to claim 7 wherein the halide is chloride and the alkali metal is potassium.

9. A method according to claim 8 wherein the fluid is an aqueous based machining fluid.

10. The method of claim 3 wherein the fluid is selected from the group consisting of an aqueous based machining fluid and an aqueous based hydraulic fluid.

11. The method of claim 10 wherein the halide is chloride and the alkali metal is potassium.

12. The method according to claim 11 wherein the fluid is an aqueous based machining fluid.

13. The method of claim 1 wherein the halide is chloride and the alkali metal is potassium.

14. The method of claim 2 wherein the halide is chloride and the alkali metal is potassium.

15. The method of claim 3 wherein the halide is chloride and the alkali metal is potassium.

* * * * *